(12) United States Patent
Edwards

(10) Patent No.: US 10,178,997 B2
(45) Date of Patent: Jan. 15, 2019

(54) HIGH-SPEED POWERED HAND TOOL WITH IMPROVED MOTOR COOLING

(71) Applicant: Gyrus ACMI, Inc., Southborough, MA (US)

(72) Inventor: Kevin C. Edwards, Olive Branch, MS (US)

(73) Assignee: Gyrus ACMI, Inc., Southborough, MA (US)

( * ) Notice: Subject to any disclaimer, the term of this patent is extended or adjusted under 35 U.S.C. 154(b) by 435 days.

(21) Appl. No.: 14/863,544

(22) Filed: Sep. 24, 2015

(65) Prior Publication Data

US 2016/0081699 A1 Mar. 24, 2016

Related U.S. Application Data

(60) Provisional application No. 62/054,455, filed on Sep. 24, 2014.

(51) Int. Cl.
*A61B 17/16* (2006.01)

(52) U.S. Cl.
CPC .. *A61B 17/1622* (2013.01); *A61B 2017/1651* (2013.01); *A61B 2217/005* (2013.01)

(58) Field of Classification Search
CPC .. A61B 17/16; A61B 17/1622; A61B 17/1628
See application file for complete search history.

(56) References Cited

U.S. PATENT DOCUMENTS

| 3,581,131 | A | 5/1971 | Cestmir |
| 3,604,960 | A | 9/1971 | Krestel |
| 4,681,540 | A | 7/1987 | Landgraf et al. |
| 5,559,380 | A | 9/1996 | Nakamura et al. |
| 6,171,300 | B1 | 1/2001 | Adams |
| 6,940,192 | B2 * | 9/2005 | Katsuzawa ............. H02K 5/04 310/52 |
| 8,533,906 | B2 | 9/2013 | Liu |
| 2002/0040229 | A1 | 4/2002 | Norman |
| 2005/0060974 | A1 | 3/2005 | Palmerton et al. |
| 2006/0156504 | A1 | 7/2006 | Bruneau |
| 2008/0020696 | A1 | 1/2008 | Van Gansen |
| 2011/0306968 | A1 | 12/2011 | Beckman et al. |
| 2013/0203014 | A1 | 8/2013 | Lieb et al. |
| 2014/0087329 | A1 * | 3/2014 | Muto ..................... A61C 1/06 433/131 |
| 2015/0201825 | A1 * | 7/2015 | Na ..................... A61B 18/1492 600/107 |

* cited by examiner

*Primary Examiner* — Christopher Beccia
(74) *Attorney, Agent, or Firm* — Pandiscio & Pandiscio

(57) ABSTRACT

A surgical device comprising: a handpiece comprising a distal end and a proximal end; a chamber formed within the handpiece; a motor disposed within the chamber; an exhaust port in fluid communication with the chamber, the exhaust port being configured for attachment to a suction source so as to apply suction to the chamber; and at least one inlet port in fluid communication with the chamber, the at least one inlet port being configured to allow ambient air to be drawn into the chamber.

12 Claims, 10 Drawing Sheets

HIGH-SPEED POWERED HAND TOOL WITH IMPROVED MOTOR COOLING

REFERENCE TO PENDING PRIOR PATENT APPLICATION

This patent application claims benefit of prior U.S. Provisional Patent Application Ser. No. 62/054,455, filed Sep. 24, 2014 by Gyrus ACMI, Inc., d.b.a. Olympus Surgical Technologies America and Kevin C. Edwards for HIGH-SPEED POWERED HAND TOOL WITH IMPROVED MOTOR COOLING, which patent application is hereby incorporated herein by reference.

FIELD OF THE INVENTION

This invention relates to surgical apparatus and procedures in general, and more particularly to high-speed powered hand tools such as high speed drills, burrs, saws, etc.

BACKGROUND OF THE INVENTION

In many surgical procedures, it is necessary or desirable to drill or abrade or cut an object, e.g., bone. In these situations, it is common to provide a high-speed powered hand tool comprising a handpiece having a high-speed electric (or pneumatic, etc.) motor, and a coupling at the distal end of the handpiece for releasably connecting a working element (e.g., a drill bit or burr or saw, etc.) to the high-speed electric (or pneumatic, etc.) motor, such that the working element (e.g., the drill bit or burr or saw, etc.) can be moved (e.g., rotated) by the high-speed electric (or pneumatic, etc.) motor and then used for the desired purpose (e.g., drilling or abrading or cutting, etc.).

See, for example, FIGS. 1 and 2, which show a high-speed powered hand tool 5 comprising a handpiece 10 having a high-speed electric (or pneumatic, etc.) motor 15 therein, and a coupling 20 at the distal end of handpiece 10 for releasably connecting a working element 25 (e.g., a drill bit or burr or saw, etc.) to high-speed electric (or pneumatic, etc.) motor 15, such that working element 25 (e.g., the drill bit or burr or saw, etc.) can be moved (e.g., rotated) by high-speed electric (or pneumatic, etc.) motor 15 and then used for the desired purpose (e.g., drilling or abrading or cutting, etc.).

It will be appreciated that, as with any electric (or pneumatic, etc.) motor, the operation of high-speed electric (or pneumatic, etc.) motor 15 generates heat. It will also be appreciated that inasmuch as high-speed electric (or pneumatic, etc.) motor 15 is disposed within handpiece 10, and inasmuch as handpiece 10 must have a limited diameter so as to be easily grasped in the hand of a clinician, the heat from high-speed electric (or pneumatic, etc.) motor 15 can build up within handpiece 10, such that it can become uncomfortable for the hand of the clinician and/or reduce the useful life of the working components of high-speed powered hand tool 5, e.g., high-speed electric (or pneumatic, etc.) motor 15.

To this end, efforts have been made to remove the heat generated by high-speed electric (or pneumatic, etc.) motor 15. By way of example but not limitation, handpiece 10 may include vents for allowing heat to dissipate from the interior of handpiece 10. However, such a "passive" approach typically has limited effectiveness. By way of further example but not limitation, a fluid (e.g., a gas or liquid) may be pumped through handpiece 10 so as to draw off the heat of high-speed electric (or pneumatic, etc.) motor 15. While such an "active" approach is typically more effective in removing heat from the interior of handpiece 10, it typically requires the provision of a supplemental pump or fan for forcing the fluid through handpiece 10 so as to draw off heat from high-speed electric (or pneumatic, etc.) motor 15. As a result, there is increased cost and complexity for the system.

The present invention provides a novel approach for cooling the motor (electric, pneumatic, etc.) of a high-speed powered hand tool without requiring the provision of a supplemental pump or fan to force a fluid (e.g., a gas or liquid) through the handpiece of the high-speed powered hand tool.

SUMMARY OF THE INVENTION

The present invention provides a novel approach for cooling the motor (electric, pneumatic, etc.) of a high-speed powered hand tool without requiring the provision of a supplemental pump or fan to force a fluid (e.g., a gas or liquid) through the handpiece of the high-speed powered hand tool.

In one preferred form of the present invention, there is provided a surgical device comprising:
   a handpiece comprising a distal end and a proximal end;
   a chamber formed within said handpiece;
   a motor disposed within said chamber;
   an exhaust port in fluid communication with said chamber, said exhaust port being configured for attachment to a suction source so as to apply suction to said chamber; and
   at least one inlet port in fluid communication with said chamber, said at least one inlet port being configured to allow ambient air to be drawn into said chamber.

In another preferred form of the present invention, there is provided a method for performing a procedure, the method comprising:
   providing a surgical device comprising:
      a handpiece comprising a distal end and a proximal end;
      a chamber formed within said handpiece;
      a motor disposed within said chamber;
      an exhaust port in fluid communication with said chamber, said exhaust port being configured for attachment to a suction source so as to apply suction to said chamber; and
      at least one inlet port in fluid communication with said chamber, said at least one inlet port being configured to allow ambient air to be drawn into said chamber;
   connecting said exhaust port to a suction source; and
   using the suction source to draw ambient air into said at least one inlet port and out said exhaust port.

In another preferred form of the present invention, there is provided a method for cooling a surgical device of the type comprising a handpiece comprising a distal end and a proximal end, a chamber formed within said handpiece, and a motor disposed within said chamber, the method comprising:
   providing an exhaust port in fluid communication with the chamber, said exhaust port being configured for attachment to a suction source so as to apply suction to said chamber, and providing at least one inlet port in fluid communication with said chamber, said at least one inlet port being configured to allow ambient air to be drawn into said chamber;
   connecting said exhaust port to a suction source; and
   using the suction source to draw ambient air into said at least one inlet port and out said exhaust port.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
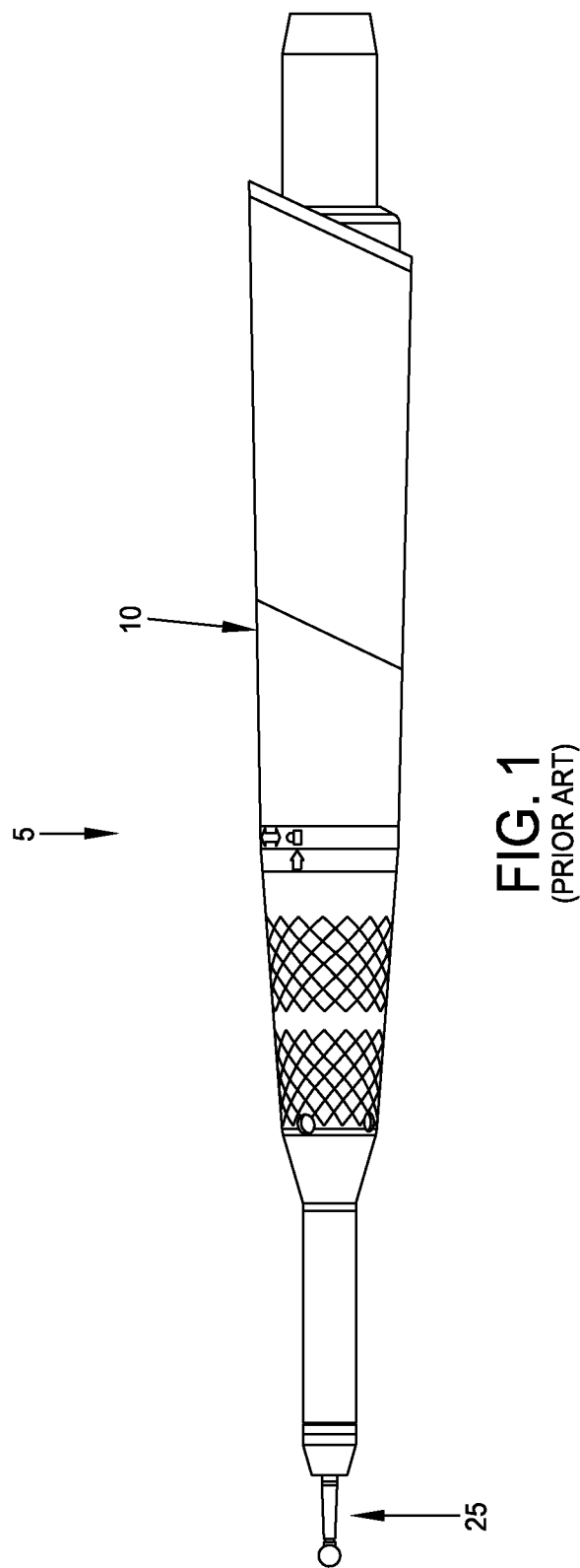
FIG. 1 is a schematic side view of a prior art high-speed powered hand tool.
Figure 2:
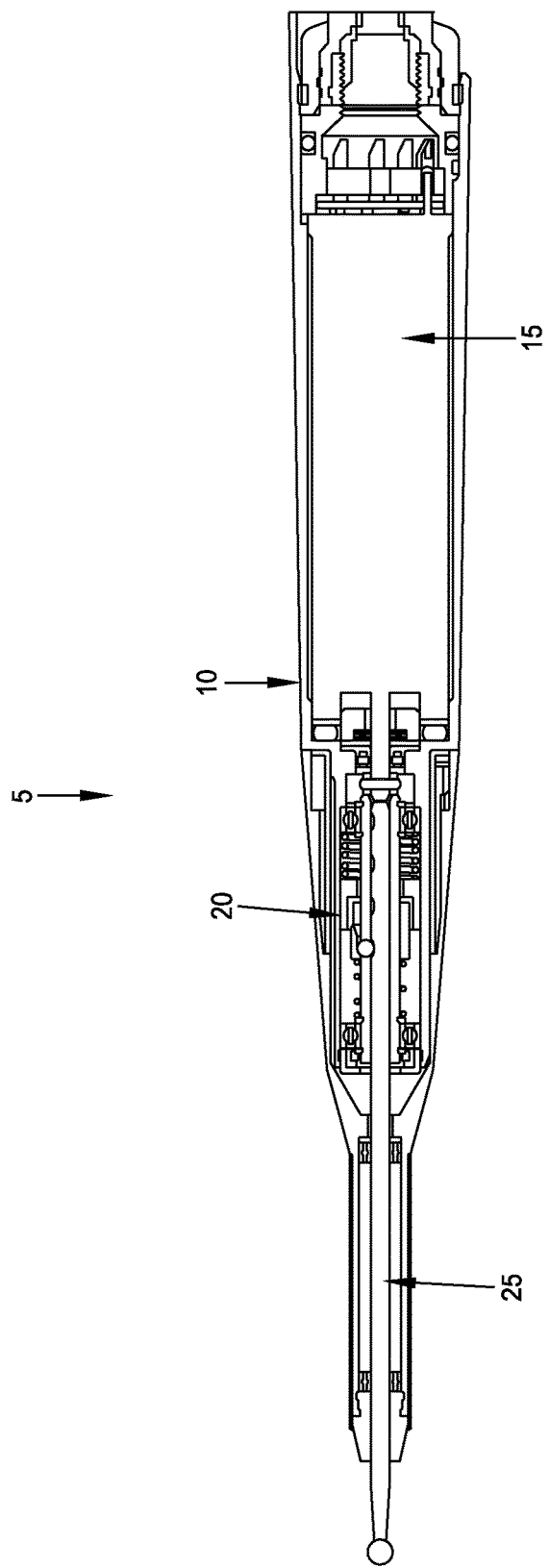
FIG. 2 is a schematic sectional view of the prior art high-speed powered hand tool shown in FIG. 1.
Figure 3:
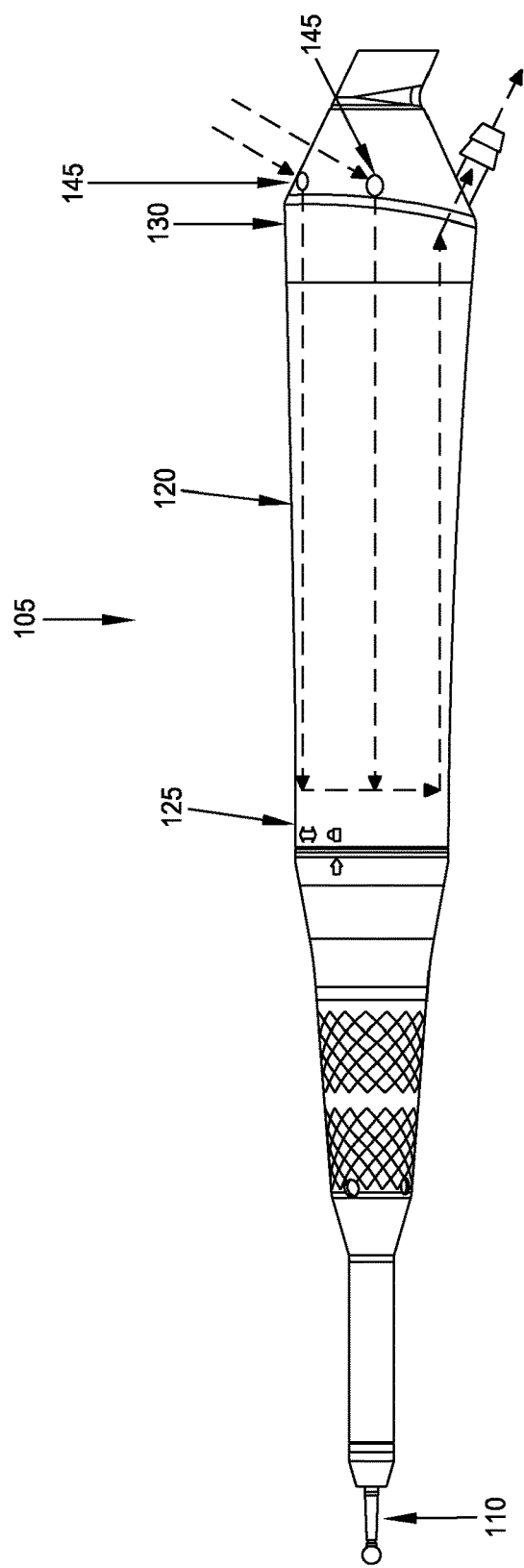
FIGS. 3-6 are schematic views showing a novel high-speed powered hand tool formed in accordance with the present invention, wherein the high-speed powered hand tool comprises novel means for cooling the electric (or pneumatic, etc.) motor contained therein.
Figure 4:
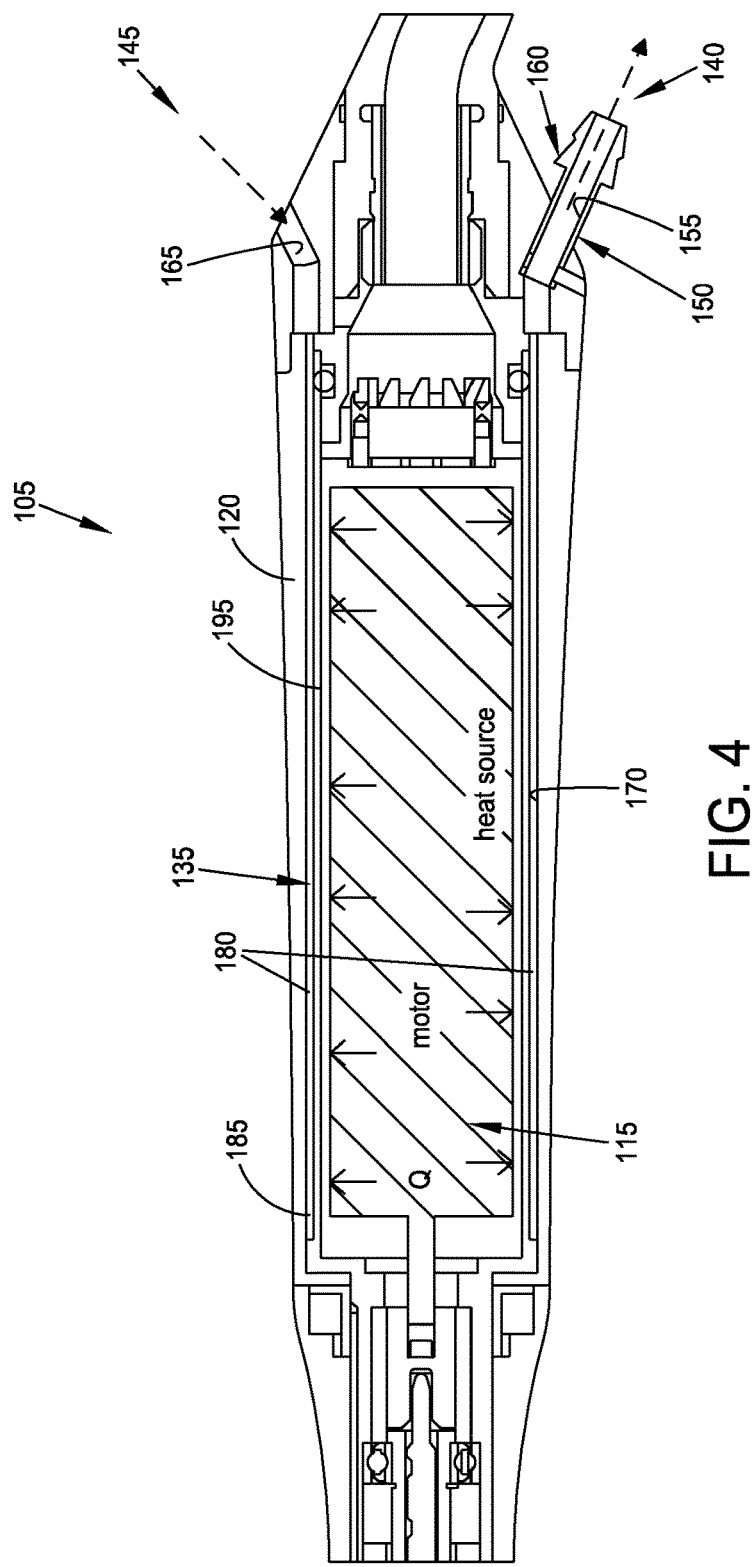
Figure 5:
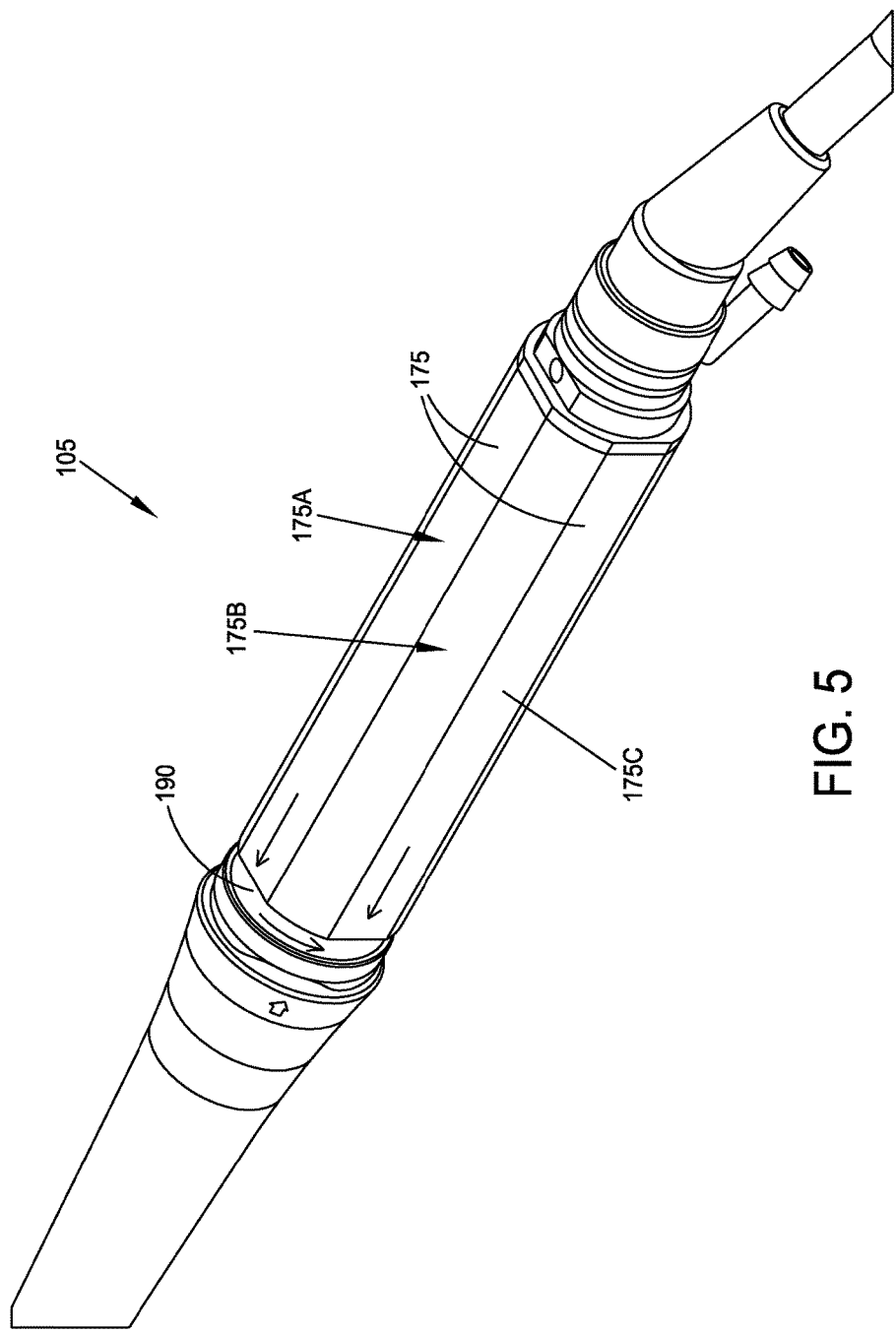
Figure 6:
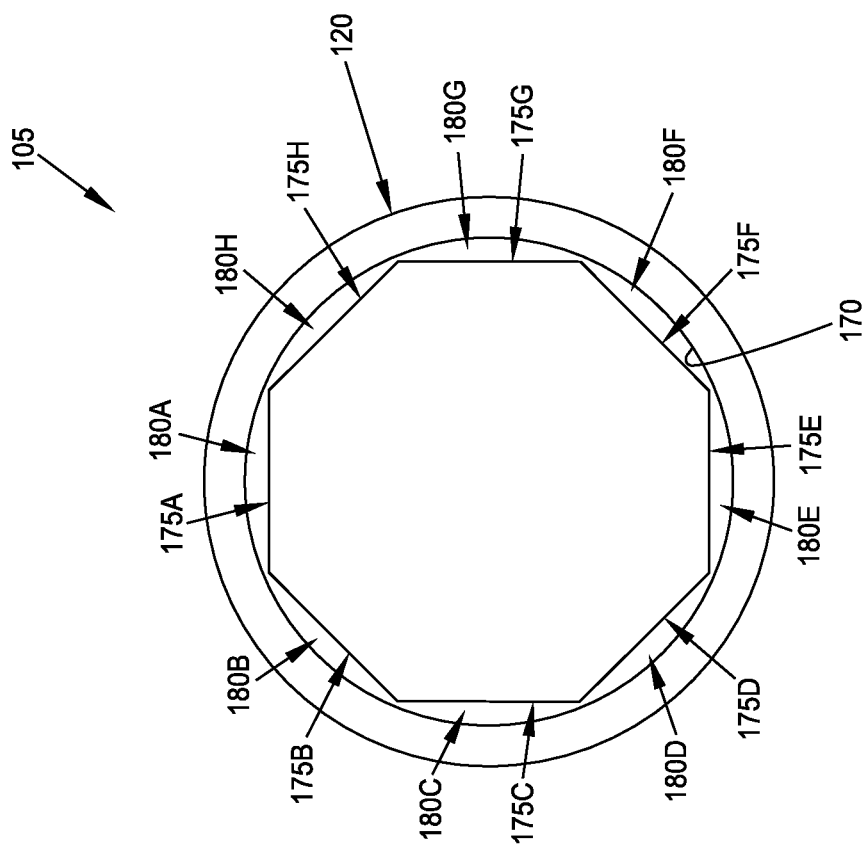

The present invention provides a novel approach for cooling the motor (electric, pneumatic, etc.) of a high-speed powered hand tool without requiring the provision of a supplemental pump or fan to force a fluid (e.g., a gas or liquid) through the handpiece of the high-speed powered hand tool.

More particularly, and looking first at FIGS. 3-6, there is shown a novel high-speed powered hand tool 105 which carries a working element 110 (e.g., a drill bit or burr or saw, etc.) which is connected to a high-speed electric (or pneumatic, etc.) motor 115, such that working element 110 (e.g., the drill bit or burr or saw, etc.) can be moved (e.g., rotated) by high-speed electric (or pneumatic, etc.) motor 115 and then used for the desired purpose (e.g., drilling or abrading or cutting, etc.).

High-speed powered hand tool 105 generally comprises a handpiece 120 comprising a distal end 125 and a proximal end 130. A chamber 135 is formed within handpiece 120. High-speed electric (or pneumatic, etc.) motor 115 is disposed within chamber 135. An exhaust port 140 is in fluid communication with chamber 135, with exhaust port 140 being configured for attachment to a suction source (not shown) so as to apply suction to chamber 135. The suction source may be a stand-alone device of the sort well known in the medical arts or, more preferably, it may be a wall suction source of the sort commonly found in healthcare facilities. At least one inlet port 145 is in fluid communication with chamber 135, with the at least one inlet port 145 being configured to allow ambient air to be drawn into chamber 135. As a result of this construction, by connecting exhaust port 140 to a suction source (not shown), ambient air may be drawn into the at least one inlet port 145, through chamber 135 and out exhaust port 140 whereby to pass ambient air around high-speed electric (or pneumatic, etc.) motor 115 and thereby cool high-speed electric (or pneumatic, etc.) motor 115. Significantly, this approach allows the motor (electric, pneumatic, etc.) of the high speed powered hand tool to be cooled without requiring the provision of a supplemental pump or fan to force a fluid (e.g., a gas or liquid) through the handpiece of the high-speed powered hand tool.

In one preferred form of the invention, exhaust port 140 comprises a hollow tube 150 which is mounted to, and projects out of, handpiece 120, wherein the lumen 155 of hollow tube 150 is in fluid communication with chamber 135. And in one particularly preferred form of the invention, hollow tube 150 is configured to receive a suction hose (not shown) connected to a suction source (not shown), e.g., hollow tube 150 comprises at least one rib 160 for retaining the suction hose on hollow tube 150.

In one preferred form of the invention, the at least one inlet port 145 comprises a plurality of inlet ports 145, and each inlet port 145 comprises a passageway 165 formed in handpiece 120 and communicating with chamber 135. And in one particularly preferred form of the invention, handpiece 120 comprises a polymeric structure, and each of the inlet ports 145 comprises a fenestration formed in the polymeric structure.

In one preferred form of the present invention chamber 135 is defined by at least one longitudinally-extending wall 170, high-speed electric (or pneumatic, etc.) motor 115 is defined by at least one longitudinally-extending wall 175, and at least one longitudinally-extending gap 180 is formed between the at least one longitudinally-extending wall 175 of high-speed electric (or pneumatic, etc.) motor 115 and the at least one longitudinally-extending side wall 170 of chamber 135. In this form of the invention, when suction is applied to exhaust port 140, ambient air is drawn into the at least one inlet port 145, along the at least one longitudinally-extending gap 180 and out exhaust port 140. Preferably the at least one longitudinally-extending gap 180 extends along substantially the entire length of high-speed electric (or pneumatic, etc.) motor 115 so as to maximize the withdrawal of heat from the electric (or pneumatic, etc.) motor.

As seen in FIGS. 3-6, in one preferred form of the invention, exhaust port 140 and the at least one inlet port 145 are both disposed at one end (e.g., at proximal end 130) of handpiece 120. And in one preferred form of the invention, the at least one longitudinally-extending gap 180 comprises at least a first longitudinally-extending gap 180 and a second longitudinally-extending gap 180, and exhaust port 140 is in fluid communication with the first longitudinally-extending gap 180, the at least one inlet port 145 is in fluid communication with the second longitudinally extending gap 180, and the first longitudinally-extending gap 180 is in fluid communication with the second longitudinally-extending gap 180 at a location which is remote from exhaust port 140 and the at least one inlet port 145 (e.g., at distal end 125). In this form of the invention, the first longitudinally-extending gap 180 is preferably in fluid communication with the second longitudinally-extending gap 180 at a manifold 185. In one preferred form of the invention, manifold 185 extends circumferentially within handpiece 120, and is preferably formed by a groove 190 formed on the exterior of high-speed electric (or pneumatic, etc.) motor 115.

It will be appreciated that, in general, it is preferred to locate exhaust port 140 at the proximal end of handpiece 120 so as to minimize inconvenience from the suction hose mounted to exhaust port 140, and to locate the at least one inlet port 145 (and preferably the plurality of inlet ports 145) at the proximal end of handpiece 120 so as to minimize the possibility of occluding the port(s) 145 by clinician hands, gloves, etc.

Preferably, the at least one longitudinally-extending wall 170 of chamber 175 comprises a single cylindrical wall, and the at least one longitudinally-extending wall 175 of high-speed electric (or pneumatic, etc.) motor 115 comprises a plurality of longitudinally-extending flat walls 175A, 175B, 175C, etc., such that a plurality of longitudinally-extending gaps 180A, 180B, 180C, etc. are formed between the plurality of longitudinally-extending flat walls 175A, 175B, 175C, etc. of high-speed electric (or pneumatic, etc.) motor 115 and the at least one longitudinally-extending wall 170 of chamber 135. Preferably each of the longitudinally-extending gaps 180A, 180B, 180C, etc. are in fluid communication with one inlet port 145 or the plurality of inlet ports 145, and each of the longitudinally-extending gaps 180A, 180B, 180C, etc. is in fluid communication with every other longitudinally-extending gap at manifold 185, and at least one of the longitudinally-extending gaps 180A, 180B, 180C, etc. is in fluid communication with exhaust port 140, such that by connecting exhaust port 140 to a suction source (not shown), ambient air may be drawn into the various inlet ports 145, along longitudinally-extending gaps 180A, 180B, 180C, etc., and out exhaust port 140, whereby to pass ambient air around high-speed electric (or pneumatic, etc.) motor 115 and thereby cool high-speed electric (or pneumatic, etc.) motor 115. In one preferred form of the invention, one inlet port 145 is in direct fluid communication with one longitudinally-extending gap 180, a second inlet port 145 is in direct fluid communication with a second longitudinally-extending gap 180, a third inlet port 145 is in direct fluid communication with a third longitudinally-extending gap 180, etc. In another preferred form of the invention, a plurality of inlet ports 145 are in direct or indirect (e.g., via a manifold) fluid communication with one or more longitudinally-extending gaps 180. In still another preferred form of the invention, a single inlet port 145 is in fluid communication with all of the longitudinally-extending gaps 180A, 180B, 180C, etc. (e.g., via a manifold).

In one preferred form of the present invention, high-speed electric (or pneumatic, etc.) motor 115 comprises a heat-conductive jacket 195 set about the exterior of high-speed electric (or pneumatic, etc.) motor 115. Heat-conductive jacket 195 may be formed integral with high-speed electric (or pneumatic, etc.) motor 115 or it may be a separate component which is united with high-speed electric (or pneumatic, etc.) motor 115 during assembly of high-speed electric (or pneumatic, etc.) motor 115 or during assembly of high-speed powered hand tool 105. In this form of the invention, heat-conductive jacket 195 comprises the aforementioned at least one longitudinally-extending flat wall 175 (and preferably comprises the aforementioned plurality of longitudinally-extending flat walls 175A, 175B, 175C, etc.), and at least one longitudinally-extending gap 180 (and preferably the plurality of longitudinally-extending gaps 180A, 180B, 180C, etc.) is (are) formed between heat-conductive jacket 190 and the at least one longitudinally-extending side wall 170 of chamber 135.

Figure 7:
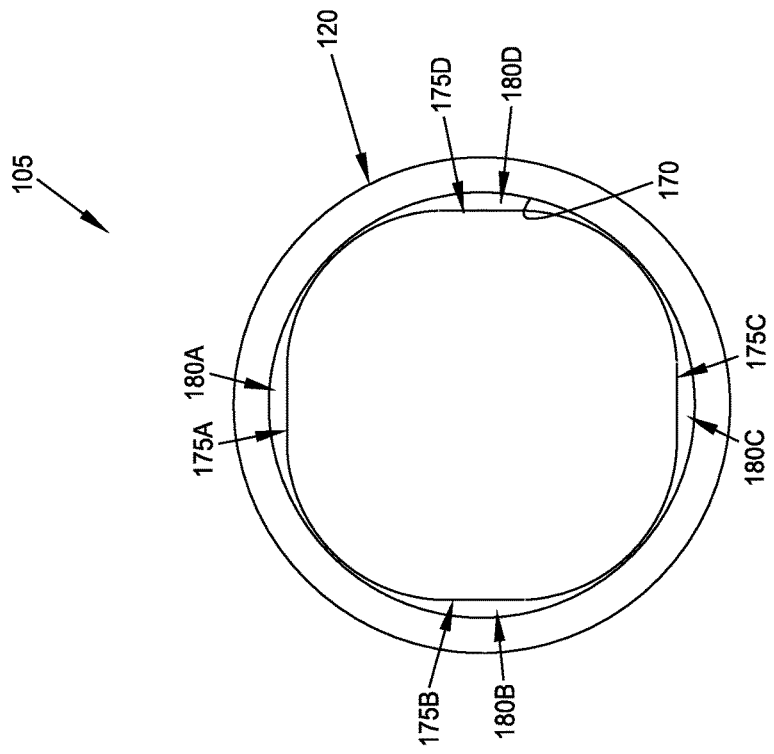
FIGS. 7 and 8 show alternative constructions for the novel high-speed powered hand tool shown in FIGS. 3-6.
Figure 8:
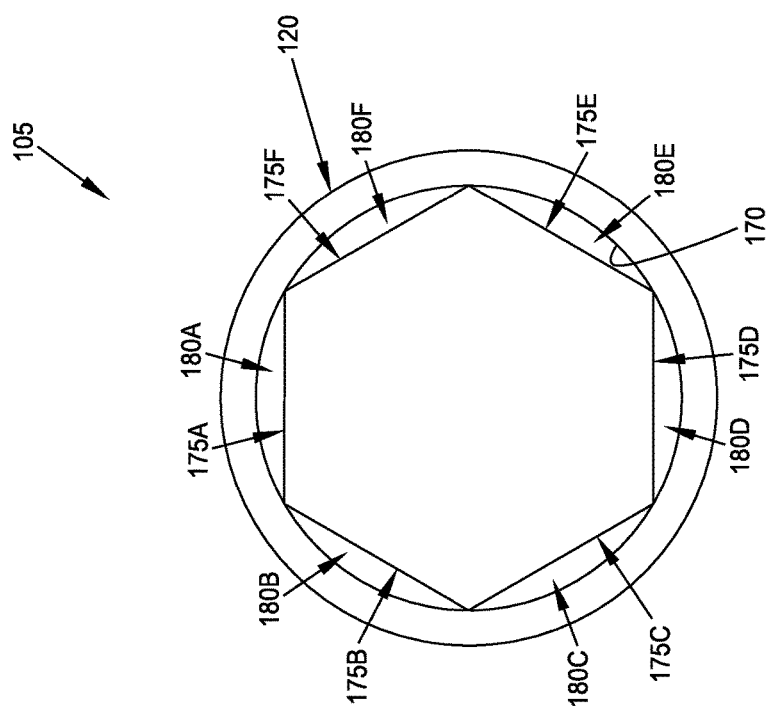

In FIGS. 3-6, the at least one longitudinally-extending flat wall 175 is shown to comprise eight longitudinally-extending flat walls 175A, 175B, 175C, etc. (whereby to create eight longitudinally-extending gaps 180A, 180B, 180C, etc.). However, it will be appreciated that other configurations may be utilized. Thus, for example, FIG. 7 shows six longitudinally-extending flat walls 175A, 175B, 175C, etc. (whereby to create six longitudinally-extending gaps 180A, 180B, 180C, etc.), and FIG. 8 shows four longitudinally-extending flat walls 175A, 175B, 175C, etc. (whereby to create four longitudinally-extending gaps 180A, 180B, 180C, etc.).

Figure 9:
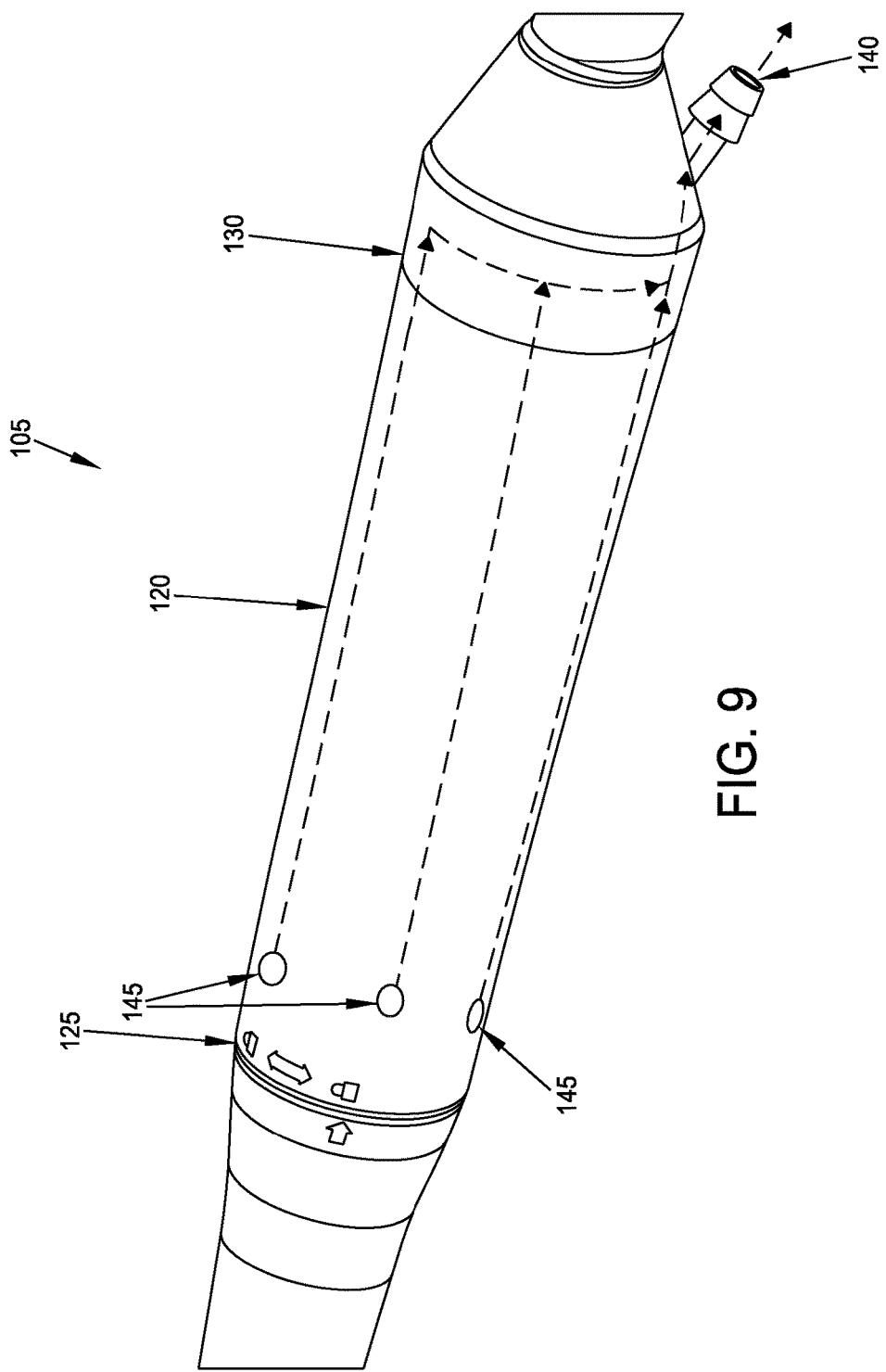
FIGS. 9-11 are schematic views showing another novel high-speed powered hand tool formed in accordance with the present invention, wherein the high-speed powered hand tool comprises alternative novel means for cooling the electric (or pneumatic, etc.) motor contained therein.
Figure 10:
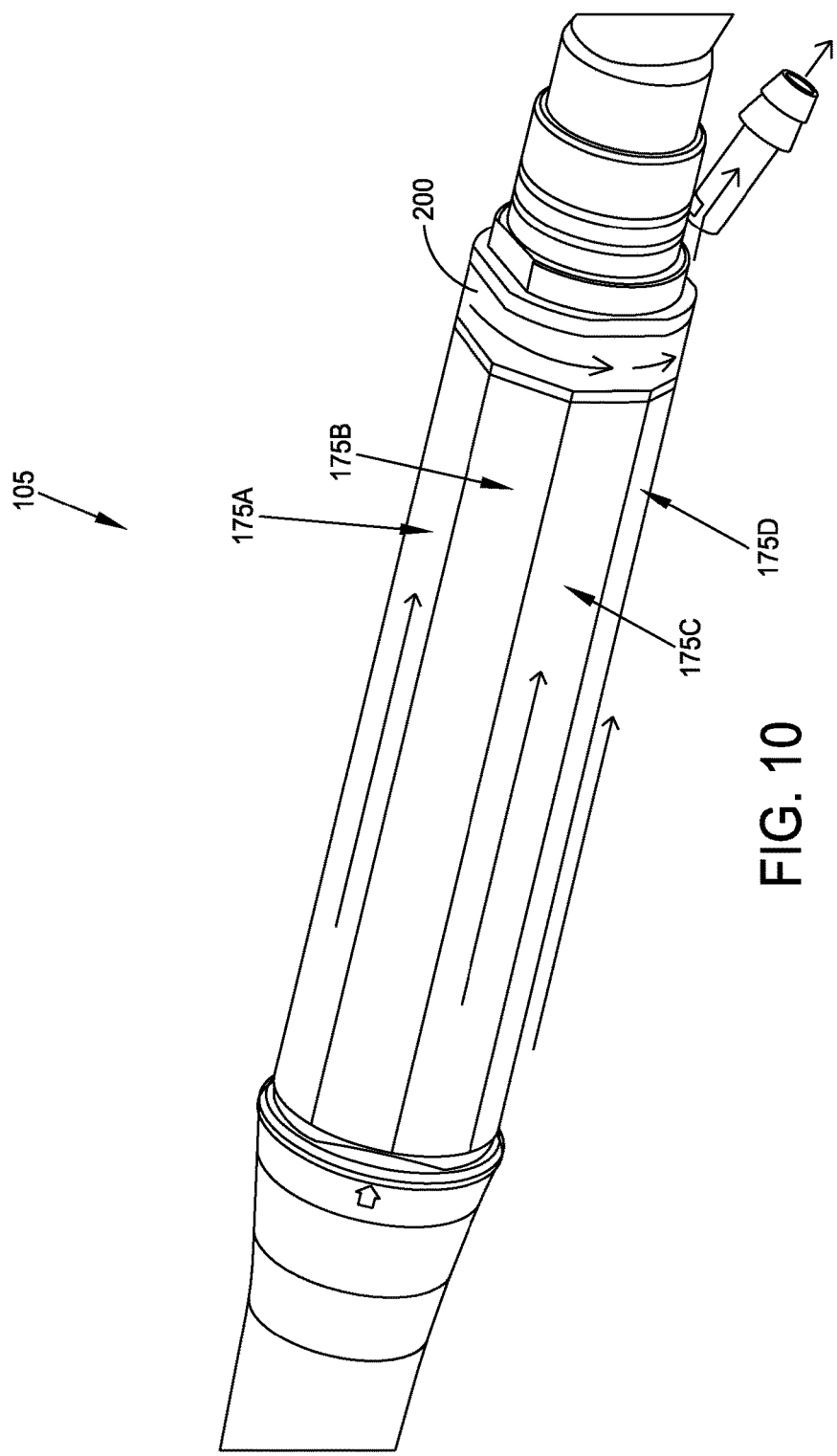
Figure 11:
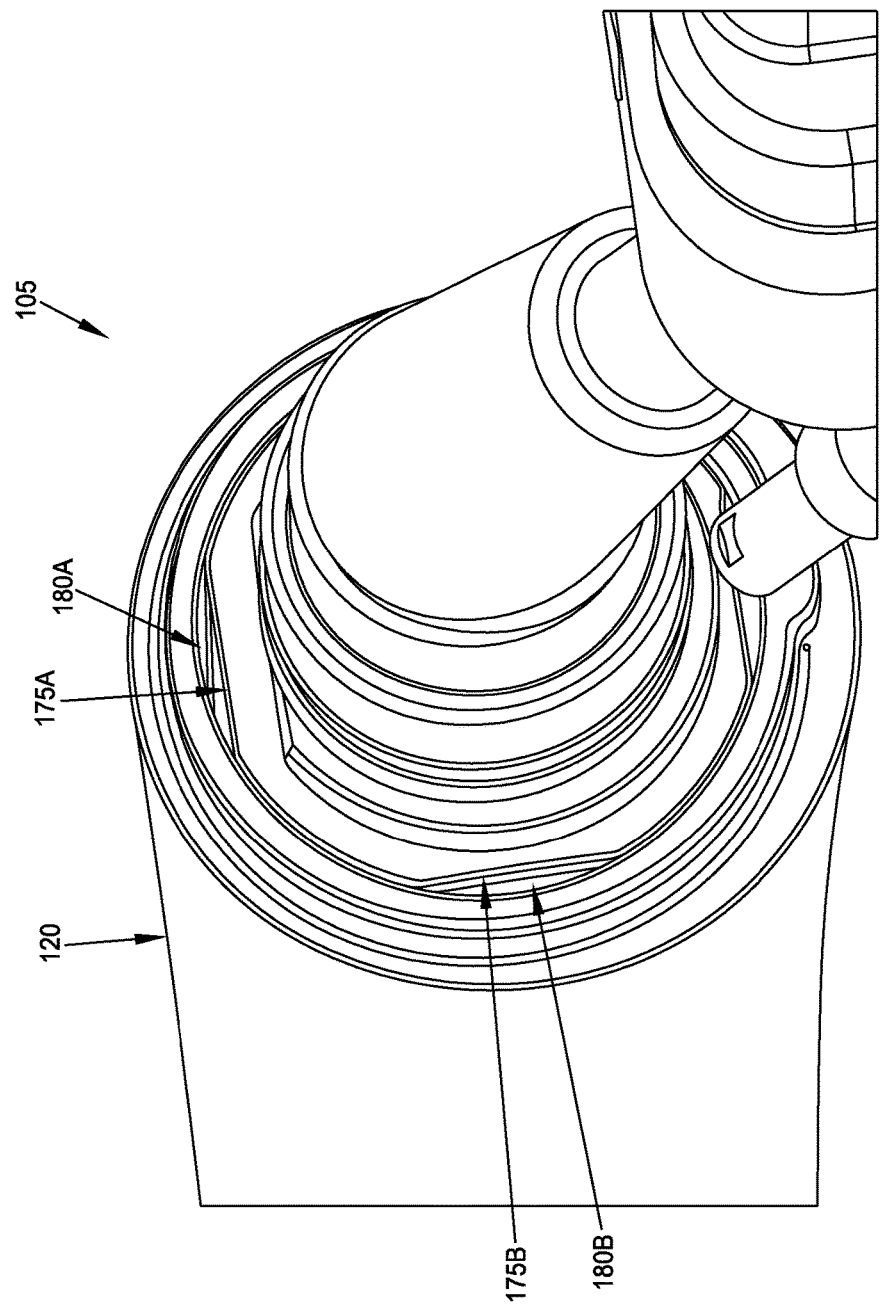

As seen in FIGS. 9-11, in another preferred form of the invention, one of exhaust port 140 and the at least one inlet port 145 is disposed at distal end 125 of handpiece 120, and the other of exhaust port 140 and the at least one inlet port 145 is disposed at proximal end 130 of handpiece 120. By way of example but not limitation, FIGS. 9-11 show exhaust port 140 disposed at proximal end 130 of handpiece 120, and the at least one inlet port 145 disposed at distal end 125 of handpiece 120. In this form of the invention, the at least one inlet port 145 preferably comprises a plurality of inlet ports 145A, 145B, 145C., etc., the at least one longitudinally-extending gap 180 preferably comprises a plurality of longitudinally-extending gaps 180A, 180B, 180C, etc., wherein inlet port 145A is in fluid communication with a longitudinally-extending gap 180, inlet port 145B is in fluid communication with a longitudinally-extending gap 180, etc., and further wherein the plurality of longitudinally-extending gaps 180A, 180B, 180C, etc., are in fluid communication with one another at a location which is remote from inlet ports 145A, 145B, 145C, etc., and further wherein at least one of the longitudinally-extending gaps 180A, 180B, 180C, etc. is in fluid communication with exhaust port 140. In one preferred form of the invention, the longitudinally-extending gaps 180A, 180B, 180C, etc. are in fluid communication with one another at manifold 196. Preferably manifold 196 extends circumferentially within handpiece 120 and is preferably formed by a groove 200 formed on the exterior of high-speed electric (or pneumatic, etc.) motor 115. As a result of this construction, by connecting exhaust port 140 to a source of suction (not shown), ambient air may be drawn into the various inlet ports 145A, 145B, 145C, etc., along longitudinally-extending gaps 180A, 180B, 180C, etc., and out exhaust port 140, whereby to pass ambient air around high-speed electric (or pneumatic, etc.) motor 115 and thereby cool high-speed electric (or pneumatic, etc.) motor 115. In one preferred form of the invention, one inlet port 145 is in fluid communication with one longitudinally-extending gap 180, a second inlet port 145 is in direct fluid communication with a second longitudinally-extending gap 180, a third inlet port 145 is in direct fluid communication with a third longitudinally-extending gap 180, etc. In another preferred form of the invention, a plurality of inlet ports 145 are in direct or indirect (e.g., via a manifold) fluid communication with one or more longitudinally-extending gaps 180. In still another preferred form of the invention, a single inlet port 145 is in fluid communication with all of the longitudinally-extending gaps 180. (e.g., via a manifold).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A surgical device comprising:
   a handpiece comprising a distal end and a proximal end;
   a chamber formed within said handpiece;
   a motor disposed within said chamber;
   an exhaust port in fluid communication with said chamber, said exhaust port being configured for attachment to a suction source so as to apply suction to said chamber; and
   at least one inlet port in fluid communication with said chamber, said at least one inlet port being configured to allow ambient air to be drawn into said chamber;
   wherein said chamber is defined by at least one longitudinally-extending wall, said motor is defined by at least one longitudinally-extending wall, and further wherein at least one longitudinally-extending gap is formed between said at least one longitudinally-extending wall of said motor and said at least one longitudinally-extending wall of said chamber;

wherein said surgical device is configured so that when suction is applied to said exhaust port, ambient air is drawn into said at least one inlet port, along said at least one longitudinally-extending gap and out said exhaust port;

wherein said exhaust port and said at least one inlet port are both disposed at one of said distal end of said handpiece and said proximal end of said handpiece; and wherein said at least one longitudinally-extending gap comprises a first longitudinally-extending gap and a second longitudinally-extending gap, and further wherein said exhaust port is in fluid communication with said first longitudinally-extending gap, said at least one inlet port is in fluid communication with said second longitudinally extending gap, and further wherein said first longitudinally-extending gap is in fluid communication with said second longitudinally-extending gap at a location which is remote from said one of said distal end of said handpiece and said proximal end of said handpiece.

2. A surgical device according to claim 1 wherein said exhaust port comprises a hollow tube mounted to and projecting out of said handpiece, wherein the lumen of said hollow tube is in fluid communication with said chamber; and wherein said hollow tube is configured to receive a suction hose connected to a suction source.

3. A surgical device according to claim 1 wherein said inlet port comprises at least one passageway formed in said handpiece.

4. A surgical device according to claim 1 wherein said surgical device is configured so that said at least one longitudinally-extending gap extends along substantially the entire length of said motor.

5. A surgical device according to claim 1 wherein said first longitudinally-extending gap is in fluid communication with said second longitudinally-extending gap at a manifold.

6. A surgical device according to claim 5 wherein said manifold extends circumferentially within said handpiece.

7. A surgical device according to claim 1 wherein said motor is defined by a plurality of longitudinally-extending flat walls, and further wherein a plurality of longitudinally-extending gaps are formed between said plurality of longitudinally-extending flat walls of said motor and said at least one longitudinally-extending wall of said chamber.

8. A surgical device according to claim 1 wherein said motor comprises a heat-conductive jacket.

9. A surgical device comprising:
a handpiece comprising a distal end and a proximal end;
a chamber formed within said handpiece;
a motor disposed within said chamber;
an exhaust port in fluid communication with said chamber, said exhaust port being configured for attachment to a suction source so as to apply suction to said chamber; and
at least one inlet port in fluid communication with said chamber, said at least one inlet port being configured to allow ambient air to be drawn into said chamber;
wherein said motor comprises a heat-conductive jacket;
wherein said chamber is defined by at least one longitudinally-extending wall, said heat-conductive jacket is defined by at least one longitudinally-extending wall, and further wherein at least one longitudinally-extending gap is formed between said at least one longitudinally-extending wall of said heat-conductive jacket and said at least one longitudinally-extending side wall of said chamber;

wherein said surgical device is configured so that when suction is applied to said exhaust port, ambient air is drawn into said at least one inlet port, along said at least one longitudinally-extending gap and out said exhaust port;

wherein said exhaust port and said at least one inlet port are both disposed at one of said distal end of said handpiece and said proximal end of said handpiece;

wherein said at least one longitudinally-extending gap comprises a first longitudinally-extending gap and a second longitudinally-extending gap, and further wherein said exhaust port is in fluid communication with said first longitudinally-extending gap, said at least one inlet port is in fluid communication with said second longitudinally extending gap, and further wherein said first longitudinally-extending gap is in fluid communication with said second longitudinally-extending gap at a location which is remote from said one of said distal end of said handpiece and said proximal end of said handpiece; and wherein said heat-conductive jacket is defined by a plurality of longitudinally-extending flat walls, and further wherein a plurality of longitudinally-extending gaps are formed between said plurality of longitudinally-extending flat walls of said heat-conductive jacket and said at least one longitudinally-extending wall of said chamber.

10. A surgical device according to claim 9
wherein said surgical device is configured so that said at least one longitudinally-extending gap extends along substantially the entire length of said heat-conductive jacket.

11. A surgical device according to claim 9 wherein said heat-conductive jacket is formed integral with at least one other element of said motor.

12. A method for performing a procedure, the method comprising:
providing a surgical device comprising:
a handpiece comprising a distal end and a proximal end;
a chamber formed within said handpiece;
a motor disposed within said chamber;
an exhaust port in fluid communication with said chamber, said exhaust port being configured for attachment to a suction source so as to apply suction to said chamber; and
at least one inlet port in fluid communication with said chamber, said at least one inlet port being configured to allow ambient air to be drawn into said chamber;
wherein said chamber is defined by at least one longitudinally-extending wall, said motor is defined by at least one longitudinally-extending wall, and further wherein at least one longitudinally-extending gap is formed between said at least one longitudinally-extending wall of said motor and said at least one longitudinally-extending side wall of said chamber;
wherein said surgical device is configured so that when suction is applied to said exhaust port, ambient air is drawn into said at least one inlet port, along said at least one longitudinally-extending gap and out said exhaust port;

wherein said exhaust port and said at least one inlet port are both disposed at one of said distal end of said handpiece and said proximal end of said handpiece; and wherein said at least one longitudinally-extending gap comprises a first longitudinally-extending gap and a second longitudinally-extending gap, and further wherein said exhaust port is in fluid communication with said first longitudinally-extending gap, said at least one inlet port is in fluid communication with said second longitudinally extending gap, and further wherein said first longitudinally-extending gap is in fluid communication with said second longitudinally-extending gap at a location which is remote from said one of said distal end of said handpiece and said proximal end of said handpiece;

connecting said exhaust port to a suction source; and using the suction source to draw ambient air into said at least one inlet port and out said exhaust port.

* * * * *